(12) United States Patent
Chen

(10) Patent No.: US 6,206,857 B1
(45) Date of Patent: Mar. 27, 2001

(54) SYRINGE WITH NEEDLE RETRACTION ARRANGEMENT

(75) Inventor: Marina Ling-Ko Chen, 550 S. Hill St., Suite 913, Los Angeles, CA (US) 90013

(73) Assignees: Marina Ling-Ko Chen; Christine Ching Yu-Ko, both of Los Angeles, CA (US)

( * ) Notice: Subject to any disclaimer, the term of this patent is extended or adjusted under 35 U.S.C. 154(b) by 0 days.

(21) Appl. No.: 09/642,946

(22) Filed: Aug. 22, 2000

(51) Int. Cl.[7] .................................................. A61M 5/00
(52) U.S. Cl. ............................................ 604/195; 604/110
(58) Field of Search ................................ 604/195, 110, 604/187, 218

(56) References Cited

U.S. PATENT DOCUMENTS

| | | | |
|---|---|---|---|
| 5,531,694 | * | 7/1996 | Clemens et al. ............... 604/110 |
| 5,632,733 | * | 5/1997 | Shaw ............................... 604/195 |
| 5,800,403 | * | 9/1998 | Pressly, Sr. et al. ............ 604/195 |
| 5,843,034 | * | 12/1998 | Redfern et al. ................ 604/195 X |

\* cited by examiner

*Primary Examiner*—John D. Yasko
(74) *Attorney, Agent, or Firm*—Raymond Y. Chan; David and Raymond Patent Group

(57) ABSTRACT

A syringe with needle retraction arrangement is adapted for automatically retracting the hollow needle into a hollow plunger after use so as to prevent the used needle from contacting with anybody. The syringe provides a closure seat at one end of a hollow plunger, wherein when the closure seat is intentionally pushed towards a mounting seat affixed in a mounting portion of a hollow barrel, a pusher member, which is detachably connect with the closure seat, presses a tip head of a hollow needle as well as an O-ring thereon to slide towards a needle hub to compress a compression spring to store a resilient force. When the engagement of the O-ring between the ring groove of the tip head and the annular wall of the O-ring passage is released, the resilient force stored in the compression spring will upwardly push the tip head of the hollow needle to press against the pusher member and breaks its connection with the closure seat to open an entrance aperture provided on the closure seat, so that the hollow needle, the pusher member and the compression spring will all be retracted into the receiving cavity of the hollow plunger automatically.

21 Claims, 6 Drawing Sheets

SYRINGE WITH NEEDLE RETRACTION ARRANGEMENT

BACKGROUND OF THE PRESENT INVENTION

1. Field of the Present Invention

The present invention relates to syringes, and more particularly to a syringe with needle retraction arrangement for automatically retracting the hollow needle into a hollow plunger after use so as to prevent the used needle from contacting with anybody.

2. Description of the Related Arts

It is well known that the needles of syringes are frequently intended for disposal after single use and rendered inoperative to prevent accidental injury or re-use with the substantial risk of cross-contamination.

U.S. Pat. Nos. 4,650,468 and 4,804,370 each suggests a kind of medical syringe that enables its used needle being retracted inside the barrel by re-pulling out the plunger. It is unpractical because the user must apply a pulling force to re-pulling out the plunger that may cause unreasonable danger to the user.

U.S. Pat. No. 4,695,274 discloses an improved kind of medical syringe which further includes a spring inside the barrel. The spring is arranged for automatically re-pulling out the plunger so as to retract the needle inside the barrel. However, the operation becomes much more difficult and troublesome because extra efforts must be applied to retain the needle's working position, i.e. extending out of the barrel.

U.S. Pat. No. 5,084,018 teaches a safety syringe having a sliding base with a hole in a barrel to hold a locking up a fix a needle cannula, in which the hole has a flange at the bottom to prevent downward sliding of the locking tip, the barrel being provided with a plurality of ventilation holes at the front end and a limiting flange at its inner wall to prevent from downward sliding of the sliding base so that the locking tip is positioned for injection, and a spring disposed at the locking tip between an end of the barrel and a needle extender so that when a hollow plunger with a cork at the top is pushed axially to the foremost position, the sliding base is forced to displace forwardly, and consequently the locking tip is forced to keep close contact with the extender and displace in an opposite direction. This kind of safety syringe substantially enables the used needle to be retracted inside the hollow plunger so that no re-pulling operation of the plunger is required. Moreover, a further push of the plunger is required to trigger the retraction of the needle. However, it also contains the following unsolved drawbacks:

(a) Both the sliding base, locking tip and the cork are simply engaged in position by means of limiting flange structure. Such engagement requires high manufacture accuracy to avoid unwanted displacement of the sliding base, the locking tip or the cork during the pushing operation of the plunger for injecting the medical liquid in the barrel. If the sliding base, the locking tip or the cork is not perfectly engaged in position, unwanted disengagement would be resulted during the injection operation that may cause unexpected injury to the patient. In order to ensure all flange engagements, very good quality control is expected and thus the manufacture cost of the 018' patent is relatively higher than usual. Furthermore, since different concentration of the medical liquid may contribute different compressing pressure against the sliding base, locking tip and the cork during the injection operation as mentioned above, a particularly kind of syringe of the 018' patent may only be applied to designated kinds of medical liquid.

(b) The retraction of the needle relies on the inwardly push of the sliding base towards the front end of the barrel, so that a space must be normally retained between the front end of the barrel and the sliding base to receive the sliding base during the retraction operation of the needle. Therefore, a plurality of ventilation holes must be provided at the front end of the barrel for air outlet. It is well known that, during medical injection, air must be absolutely prevented from injecting into a human body. Although high quality of airtight sealing can be provided between the barrel and the sliding base, it is still unreasonable to expose the patient to any kind of such risk.

U.S. Pat. No. 5,782,804 suggests a fluid handling device having a needle retraction assembly which brings about the retraction of a hollow needle after use, wherein a movable sleeve member is provided to substitute the sliding base in the above mentioned 018' patent, and an annular space communicating with outside is formed so that the air space between the sliding base and the front end of the barrel and the air ventilation holes provided on the front end of the barrel as suggested in the 018' patent are eliminated. However, this 804' patent also creates the following new drawbacks at the same time.

(a) As shown in FIGS. 6 and 9 of the 804' patent, some medical liquid will be left in the space formed between the end wall of the piston and the front end of the body portion when the piston is fully pushed before the needle is retracted. In other words, the medicine being actually injected is less than the required dose of medicine.

(b) The engagement between the sleeve member 36 and the needle end portion 18 must be firmer than the engagement between the sleeve member 36 and the annular wall portion 32 of the barrel, so that when the sleeve member 36 is downwardly pressed by the piston 6, the needle end portion 18 will downwardly move with the sleeve member 36 and compress the spring 28, as shown in FIG. 9. However, it is unreasonable that when the sleeve member 36 is pushed to the bottom position as shown in FIG. 10, the spring 28 will push up the needle and the needle end portion 18 to retract upwardly into the hollow piston 6 without driving the sleeve member 36 upwards at the same time.

SUMMARY OF THE PRESENT INVENTION

The main object of the present invention is to provide a syringe with needle retraction arrangement for automatically retracting the hollow needle into a hollow plunger after use so as to prevent the used needle from contacting with anybody.

Another object of the present invention is to provide a syringe with needle retraction arrangement which is easy to assembly and has a relatively low manufacturing cost.

Another object of the present invention is to provide a syringe with needle retraction arrangement, wherein no air ventilation holes or air space is required in the structure.

In order to accomplish the above objects, the present invention provides a syringe with needle retraction arrangement, which comprises:

a hollow barrel having an open end portion, a needle mounting portion, and a tubular needle hub extending from the needle mounting portion to provide a needle passageway therethrough and an end shoulder radically extended inwardly from a free end of the needle mounting portion, a hollow needle having a tissue penetrating end and a tip end thereof affixed with a cylindrical tip head which has a shallow ring groove provided thereon, wherein the tip head of the hollow needle is disposed in the needle mounting portion with the tissue penetrating end penetrating through the needle passageway, a compression spring surrounding the hollow needle and having two ends pressing against the end shoulder of the needle hub and the tip head of the hollow needle respectively, an O-ring removably resting around the ring groove of the tip head, a mounting seat, which is integrally affixed within the needle mounting portion, having an O-ring passage coaxially aligned with the needle passageway of the needle hub, a top end portion of the O-ring passage reducing diameter to form a stopper shoulder against which the O-ring abuts, wherein a circular gap is formed between the ring groove of the tip head of the hollow needle and an annular wall of the O-ring passage, the circular gap having a width smaller than a diameter of the O-ring so as to compress the O-ring between the stopper shoulder and the ring groove and to securely mount the tip head in the O-ring passage, and a hollow plunger adapted to travel through the hollow barrel, the hollow plunger having an outer close end and an inner end inserted in the hollow barrel through the open end portion, a closure seat being connected to the inner end of the hollow plunger so as to define a receiving cavity inside the hollow plunger, the closure seat having an entrance aperture positioned above the O-ring passage of the mounting seat, the entrance aperture being covered by a pusher member which is circumferentially connected with the entrance aperture in such a manner that the pusher member is detached to open the entrance aperture when a predetermined pound of urging force is applied to the pusher member.

Therefore, when the closure seat of hollow plunger is intentionally pushed towards the mounting seat, the pusher member presses the tip head as well as the O-ring thereon to slide towards the needle hub and further compress the compression spring to store a resilient force. The present invention is arranged in such a manner that when the O-ring is pressed to travel through of the O-ring passage, the resilient force of the compression spring will be increased to a force larger than the predetermined pound of urging force. At this moment, the engagement of the O-ring between the ring groove of the tip head and the annular wall of the O-ring passage is released, wherein the resilient force stored in the compression spring will upwardly push the tip head of the hollow needle to press against the pusher member and breaks its connection with the closure seat to open the entrance aperture, so that the hollow needle, the pusher member and the compression spring will all be retracted into the receiving cavity of the hollow plunger automatically.

DETAILED DESCRIPTION OF THE PREFERRED EMBODIMENT

Figure 1:
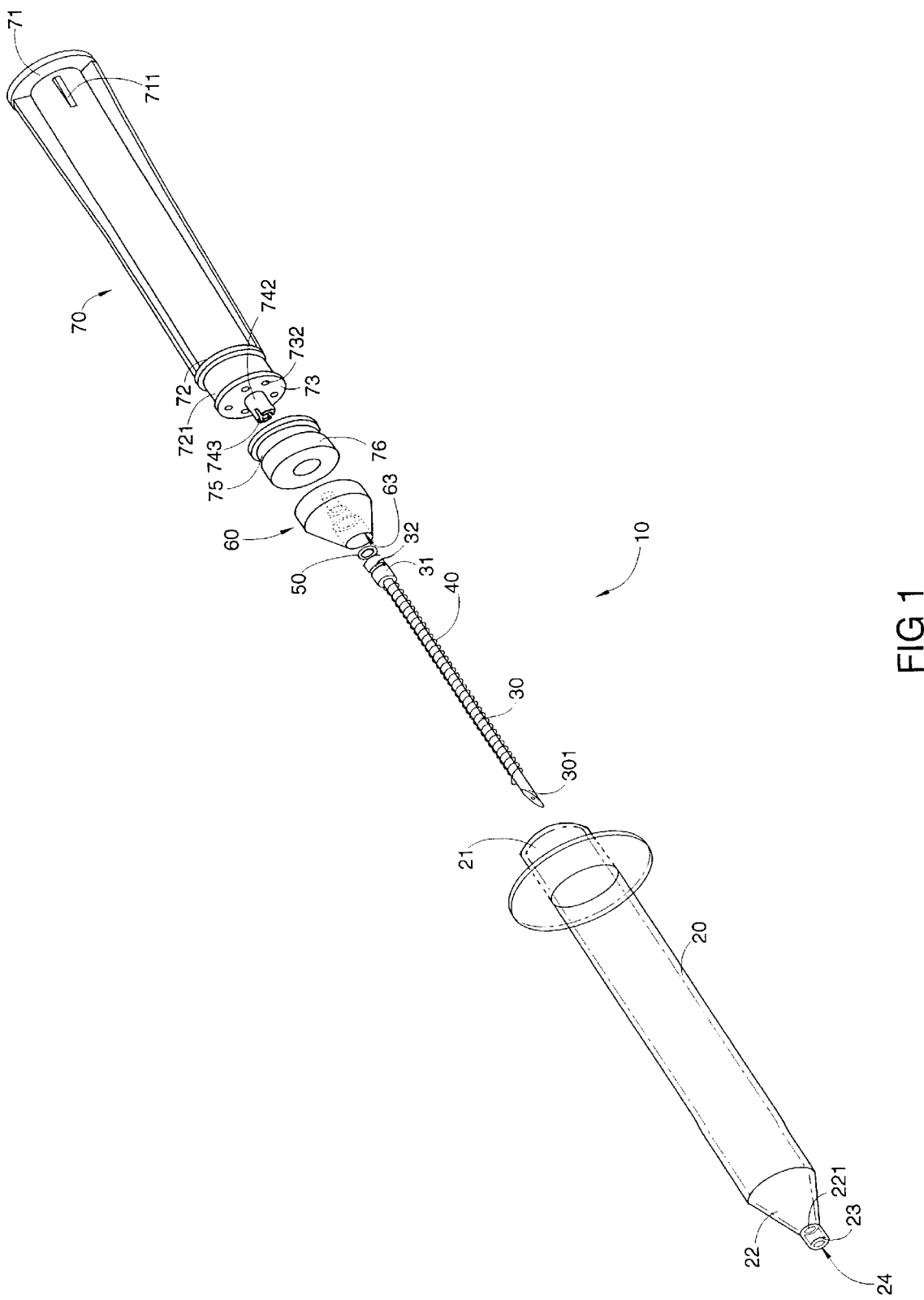
FIG. 1 is an exploded perspective view of a syringe with needle retraction mechanism according to preferred embodiment of the present invention.

Referring to FIGS. 1 to 5, a syringe 10 with needle retraction arrangement according to a preferred embodiment of the present invention is illustrated, which comprises a hollow barrel 20, a hollow needle 30, a compression spring 40, an O-ring 50, a mounting seat 60, and a hollow plunger 70.

Figure 2:
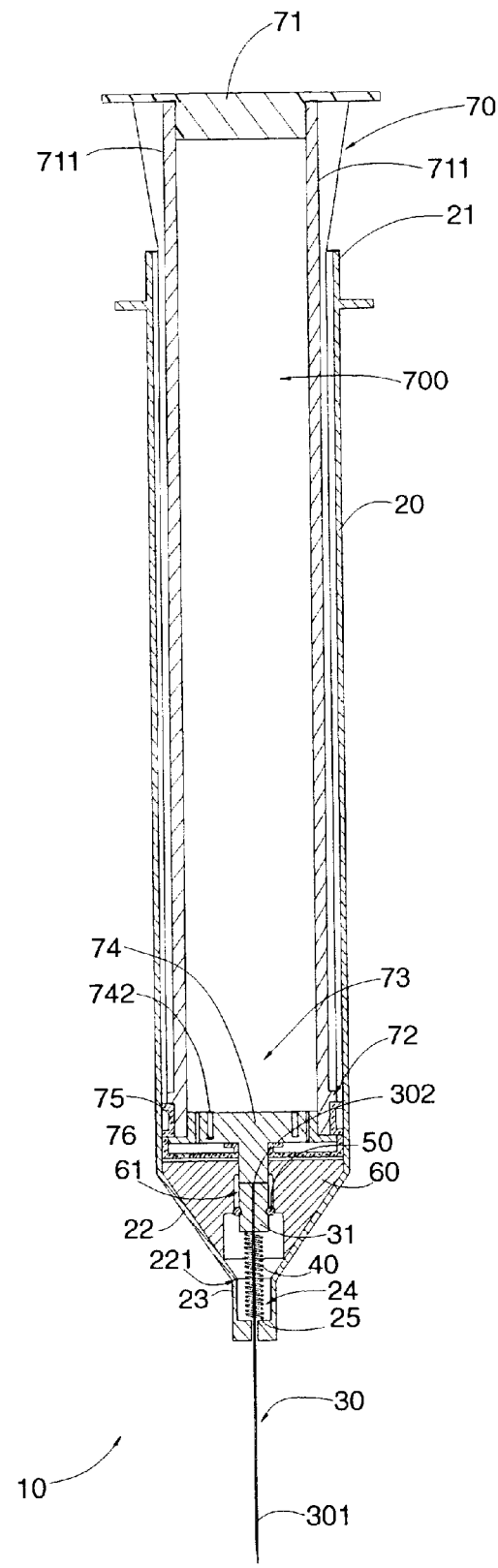
FIG. 2 is a sectional view of the syringe, while it is empty, according to the above preferred embodiment of the present invention.

The hollow barrel 20 has an open end portion 21, a needle mounting portion 22, and a tubular needle hub 23 extending from the needle mounting portion 22 to provide a needle passageway 24 therethrough and an end shoulder 25 radically extended inwardly from a free end 221 of the needle mounting portion 22, as shown in FIGS. 1 and 2.

The hollow needle 30 has a tissue penetrating end 301 and a tip end 302 thereof affixed with a cylindrical tip head 31 which has a shallow ring groove 32 provided thereon for the O-ring 50 removably resting therearound, wherein the tip head 31 of the hollow needle 30 is disposed in the needle mounting portion 22 with the tissue penetrating end 31 penetrating through the needle passageway 24.

Figure 3:
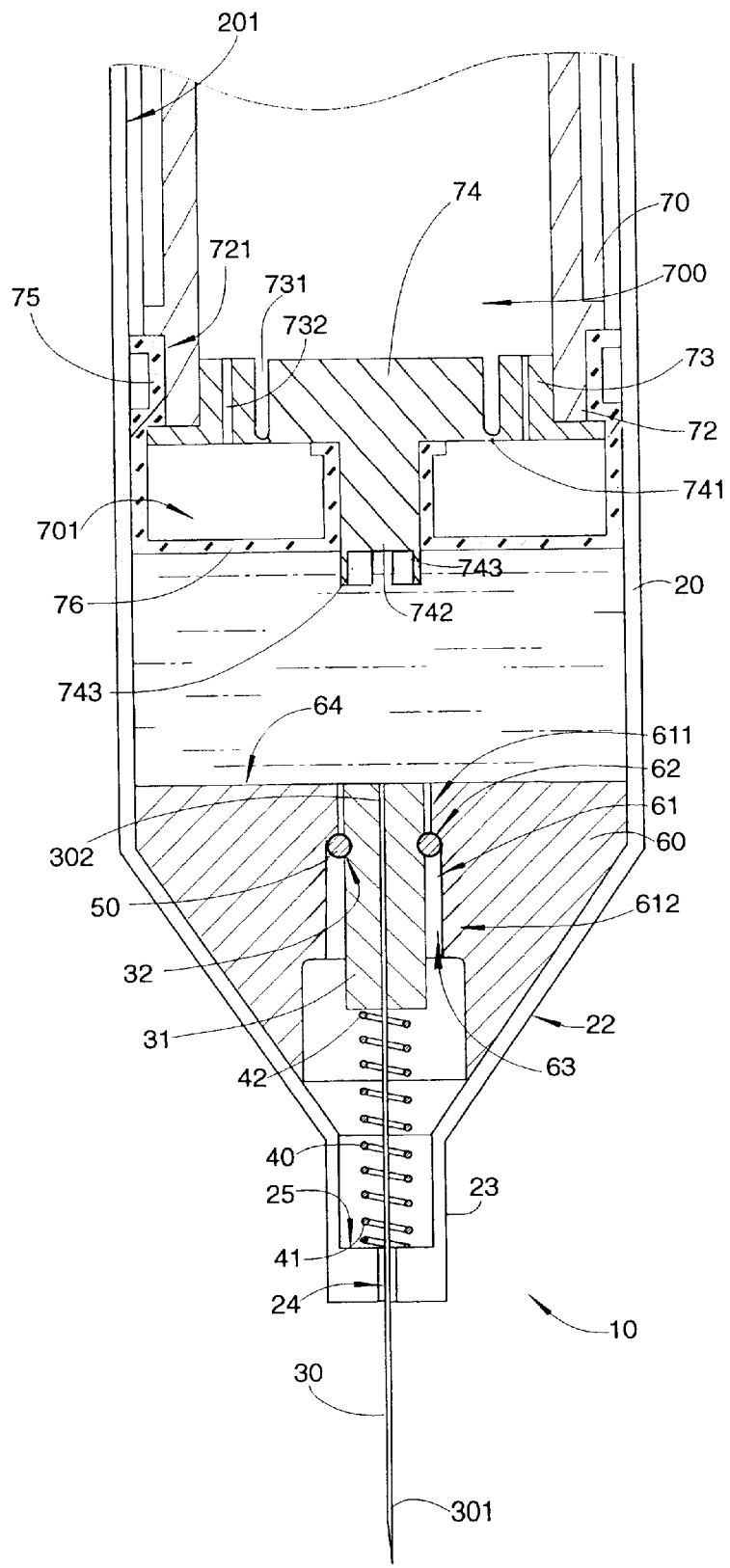
FIG. 3 is a partial sectional view of the syringe, while it is filled with medicine, according to the above preferred embodiment of the present invention.
Figure 4:
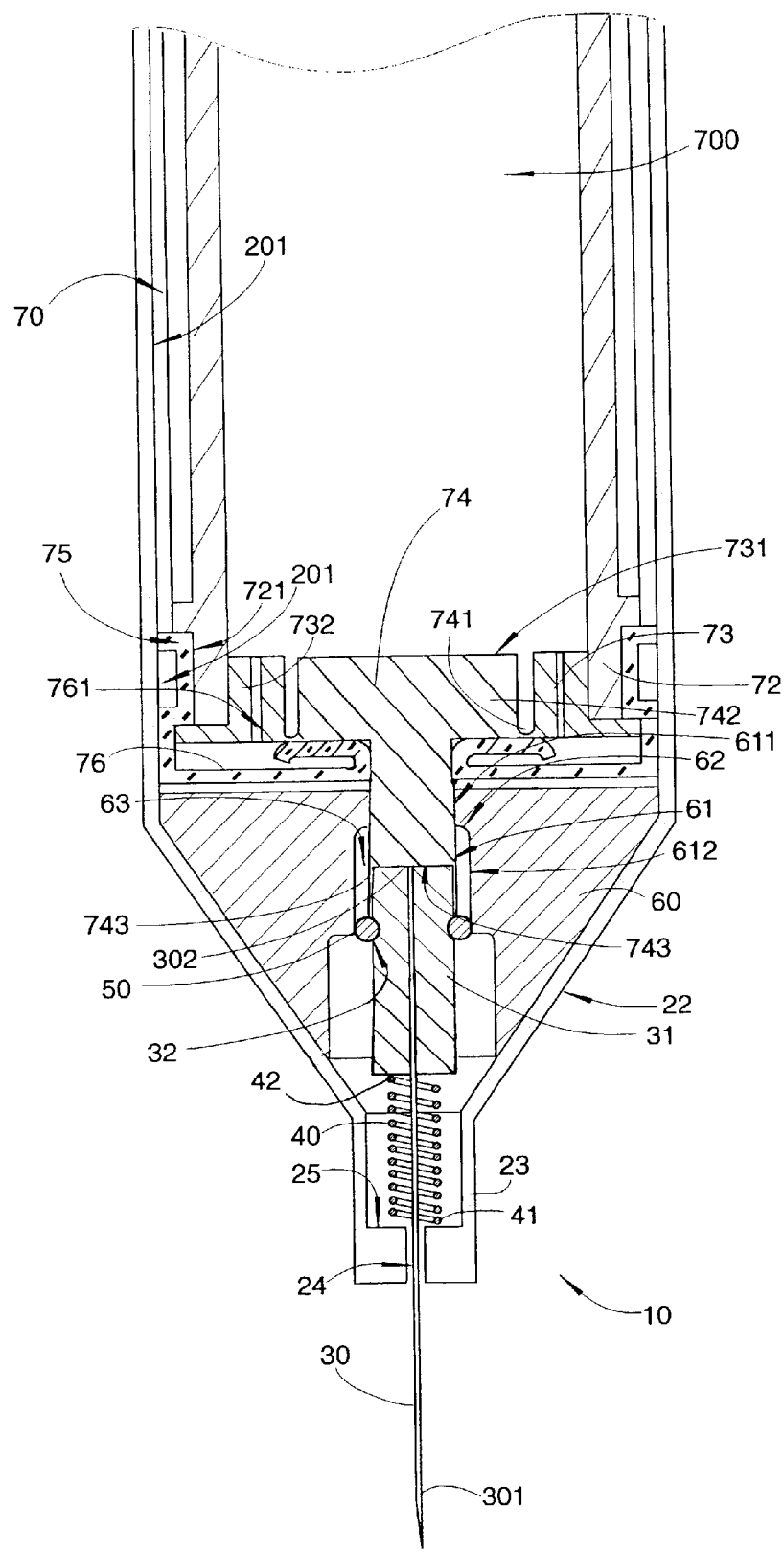
FIG. 4 is a partial sectional view of the syringe according to the above preferred embodiment of the present invention, illustrating how the pusher member pressing against the tip head of the needle.

The compression spring 40 which is arranged surrounding the hollow needle 30 has two ends 41, 42 pressing against the end shoulder 25 of the needle hub 24 and the tip head 31 of the hollow needle 30 respectively, as shown in FIGS. 3 and 4.

The mounting seat 60, as shown in FIGS. 3 and 4, which is integrally affixed within the needle mounting portion 22, has an O-ring passage 61 coaxially aligned with the needle hub 23, a top end portion 611 of the O-ring passage 61 reducing diameter to define a stopper shoulder 62 against which the O-ring 50 abuts, wherein a circular gap 63 is formed between the ring groove 32 of the tip head 31 of the hollow needle 30 and an annular wall 612 of the O-ring passage 61, the circular gap 63 having a width smaller than a diameter of the O-ring 50 so as to compress the O-ring 50 between the stopper shoulder 62 and the ring groove 32 and to securely mount the tip head 31 in the O-ring passage 61.

The hollow plunger 70, which is adapted to coaxially travel through the hollow barrel 20, has an outer close end 71 and an inner end 72. The outer close end 71 has a plurality of air holes 711 provided thereon, as shown in FIGS. 1 and 2. The inner end 72 is inserted in the hollow barrel 20 through the open end portion 21, a closure seat 73 being connected to the inner end 72 of the hollow plunger 70 so as to define a receiving cavity 700 inside the hollow plunger 70.

Figure 5:
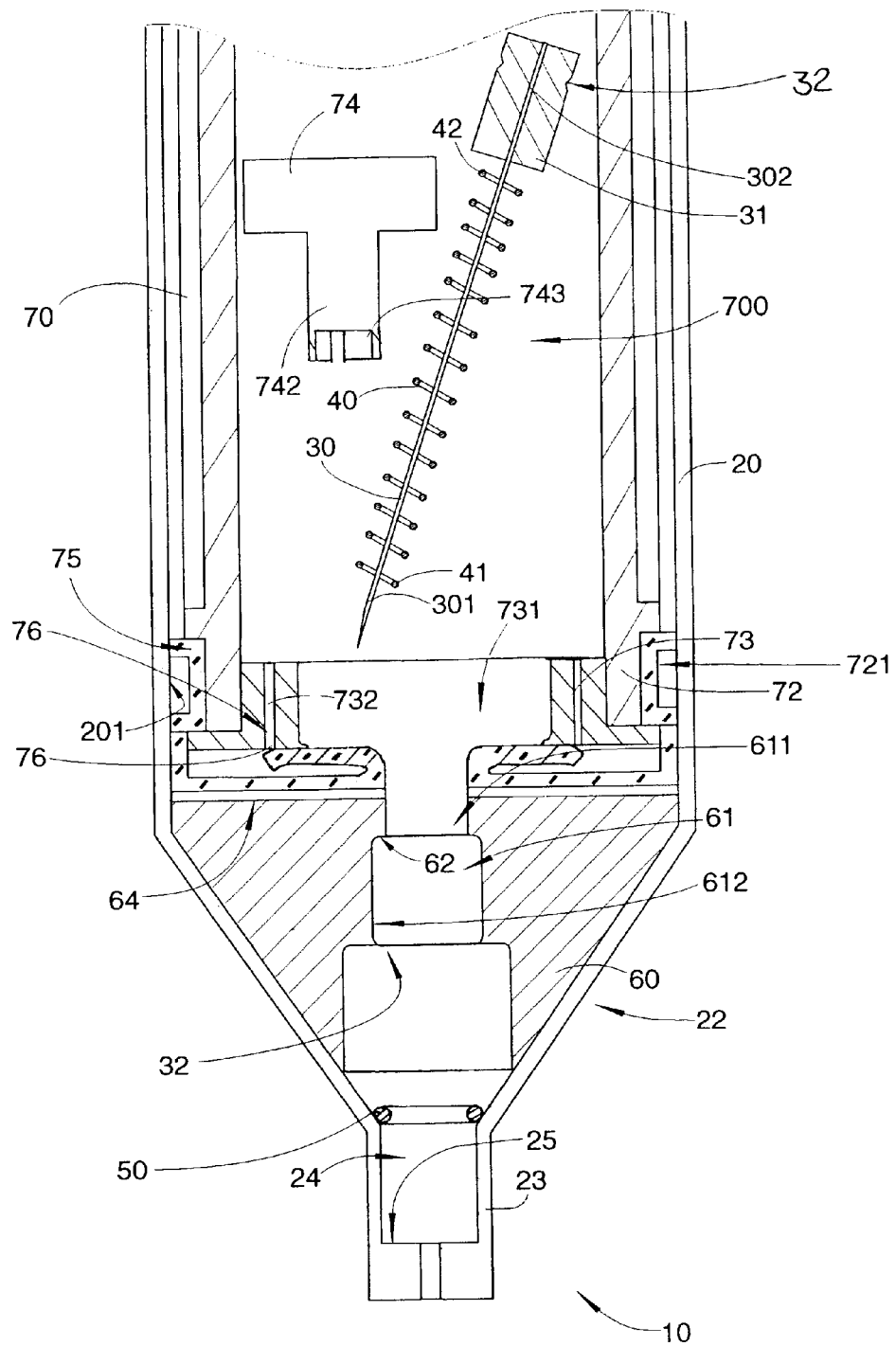
FIG. 5 is a partial sectional view of the syringe, while its needle is retracted inside the plunger, according to the above preferred embodiment of the present invention.

As shown in FIGS. 3, 4 and 5, the closure seat 73 has an entrance aperture 731 positioned above the O-ring passage 61 of the mounting seat 60 and a plurality of air apertures 732 provided around the entrance aperture 731. The entrance aperture 731 is covered by a pusher member 74 which is circumferentially connected with the entrance aperture 731 through a circular thin connecting rib 741 in such a manner that, the thin pusher member 74 is detached to open the entrance aperture 731 when a predetermined pound of urging force is applied to the pusher member 74 and breaks the connecting rib 741.

Therefore, when the closure seat 73 of hollow plunger 70 is intentionally pushed towards the mounting seat 60, the pusher member 74 presses the tip head 31 as well as the O-ring 50 thereon to slide towards the needle hub 23 and further compress the compression spring 40 to store a resilient force.

According to the preferred embodiment of the present invention, the pusher member 74 further comprises a pushing stud 742 protruded towards the mounting seat 60 and a plurality of pressing wings 743 spacedly extended from the pushing stud 742 downwardly. The pushing stud 742 has a size adapted to enter the O-ring passage 61 and directly apply pressing force onto the tip head 31 of the needle 30 when the plunger 70 is inwardly pushed towards the mounting seat 60.

As shown in FIGS. 3 to 5, a sealing groove 721 is provided around the inner end 72 for holding a ring shaped sealing member 75 thereon. The sealing member 75, which is made of elastic material such as rubber, fits in the clearance between an inner annular wall 201 of the barrel 20 and the sealing groove 721 so as to ensure air tight and sealing effects of the plunger 70.

The closure seat 73 further comprises a spacer 76 disposed below a bottom surface of the closure seat 73 and extended surrounding the pushing stud 742 of the pusher member 74, wherein an air layer 761 is defined between the bottom surface of the closure seat and the spacer 76.

According to the preferred embodiment of the present invention, as shown in FIGS. 3 to 5, the spacer 76 is integrally extended downwardly from a bottom end of the sealing member 75 to form a U-shaped body.

As shown in FIG. 3, the liquid form medicine 80 is sucked in through the hollow needle 30 to fill between plunger 70 and the mounting seat 60 inside the barrel 20. When the plunger 70 is pushed down gradually, the medicine 80 is pushed to eject through the hollow needle 30 which is penetrated into a patient's tissue. As shown in FIG. 2, when the plunger 70 is fully pushed down until the spacer 76 is in contact with a top surface 64 of the of the mounting seat 60, all medicine is ejected and then the needle 30 can be withdrawn from the patient's tissue. At this moment, the pressing wings 743 are inserted into the top end portion 611 of the O-ring passage 61 and in contact with O-ring 50.

After the user completely pulls out the needle 30 from the patient, the user can immediately apply an additional force to push in the plunger 70 that will deform the spacer 76 and compress the air layer 761, wherein the air inside the air layer 761 may escape through the air apertures 732 into the receiving cavity 700 of the plunger 70. Therefore, the pushing stud 742 can thus be further downwardly pressed against the tip head 31 of the needle 30 to push the tip head 31 and compress the compression spring 40 to store a resilient force, as shown in FIG. 4. At the same time, the pressing wings 743 will also be downwardly pressed against the O-ring 50 rested around the ring groove 32 towards the needle hub 23.

According to the preferred embodiment of the present invention, as shown in FIGS. 4 and 5, the engagement of tip head 31 within the O-ring passage 61 is arranged in such a manner that, after the O-ring 50 is pushed by the pressing wings 743 to travel through of the O-ring passage 61, the compression spring 40 can be continuously compressed until its resilient force is increased to a force larger than the predetermined pound of urging force required to break the connecting rib 741. At this moment, the O-ring is pushed out of the O-ring passage 61 so that the engagement of the O-ring 50 between the ring groove 32 of the tip head 31 and the annular wall 612 of the O-ring passage 61 is released. Then, the resilient force stored in the compression spring 40 will upwardly push the tip head 31 of the hollow needle 30 to press against the pusher member 74 until its connecting rib 741 is broken to open the entrance aperture 731 of the closure seat 73, shown in FIG. 5, so that the hollow needle 30, the pusher member 74 and the compression spring 40 will all be retracted into the receiving cavity 700 of the hollow plunger 70 automatically.

Figure 6:
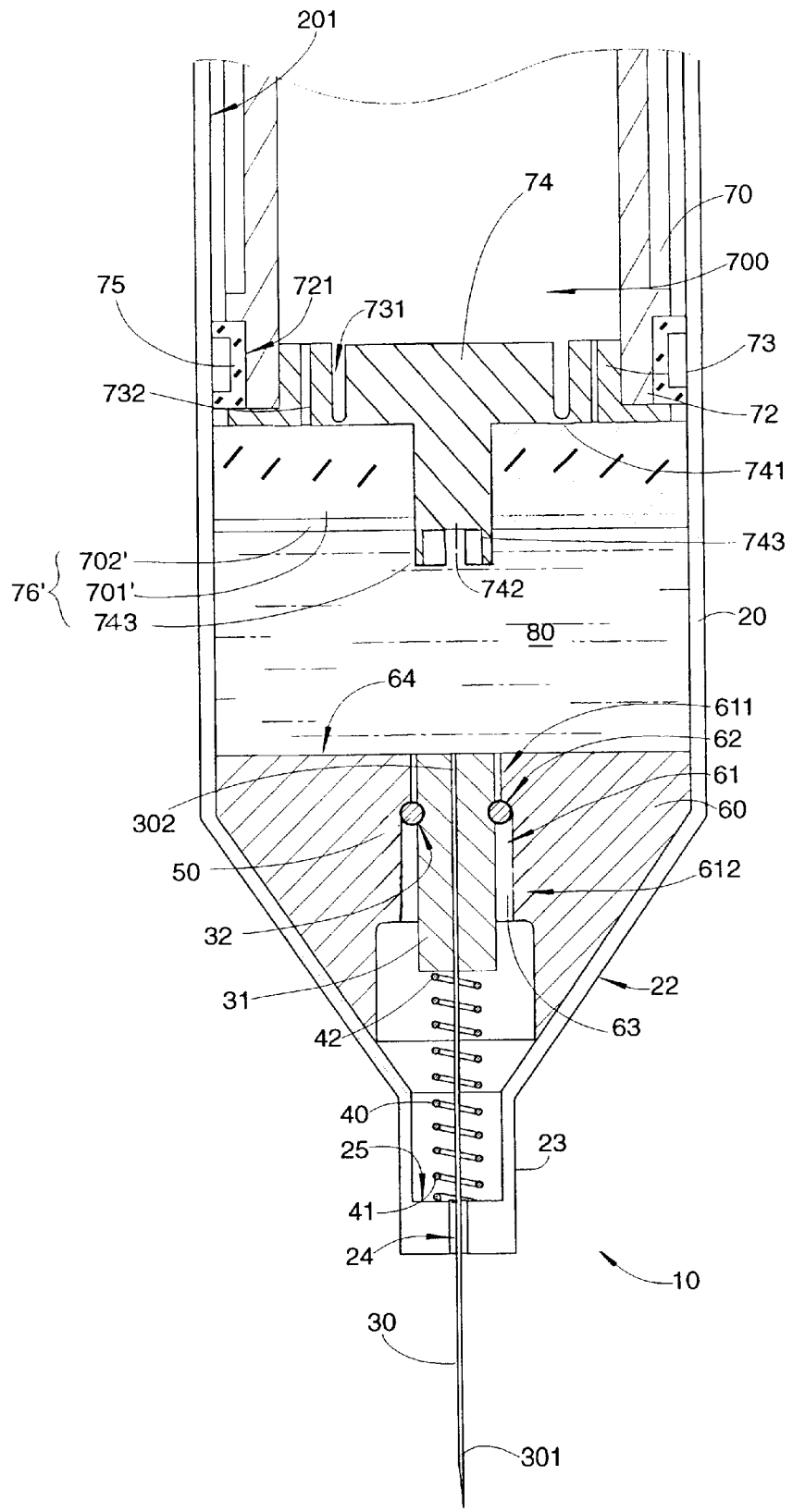
FIG. 6 is a partial sectional view of a syringe according to an alternative mode of the above referred embodiment of the present invention.

Referring to FIG. 6, an alternative mode of the syringe according to the above preferred embodiment of the present invention is illustrated, wherein the spacer 76 of the above preferred embodiment is substituted by an alternative spacer 76' which comprises a deformable washer member 761' and a plastic made pusher ring 762' integrally attached to a bottom surface of the washer member 761'. The deformable washer member 761' is made of foaming material so that it is capable of reducing its thickness under axial compression. The spacer 76' has a thickness equal to a length of the pushing stud 742 so as to positioned around the pushing stud 742 by attaching a top side of the washer member 761' to a bottom surface of the closure seat 73.

Accordingly, the syringe 10 as disclosed in the present invention can be easily operated to retract the hollow needle 30 into a hollow plunger 70 after use so as to prevent the used needle 30 from contacting with anybody. Moreover, the syringe 10 is easy to assembly and has a relatively low manufacturing cost.

What is claimed is:

1. A syringe, comprising:

a hollow barrel having an open end portion, a needle mounting portion, and a tubular needle hub extending from said needle mounting portion to provide a needle passageway therethrough and an end shoulder radically extended inwardly from a free end of said needle mounting portion;

a hollow needle having a tissue penetrating end and a tip end thereof affixed with a cylindrical tip head which has a shallow ring groove provided thereon, wherein said tip head of said hollow needle is disposed in said needle mounting portion with said tissue penetrating end penetrating through said needle passageway;

a compression spring surrounding said hollow needle and having two ends pressing against said end shoulder of said needle hub and said tip head of said hollow needle respectively;

an O-ring removably resting around said ring groove of said tip head;

a mounting seat, which is integrally affixed within said needle mounting portion, having an O-ring passage coaxially aligned with said needle passageway of said needle hub, a top end portion of said O-ring passage reducing diameter to form a stopper shoulder against which said O-ring abuts, wherein a circular gap is formed between said ring groove of said tip head of said hollow needle and an annular wall of said O-ring passage, said circular gap having a width smaller than a diameter of said O-ring so as to compress said O-ring between said stopper shoulder and said ring groove and to securely mount said tip head in said O-ring passage; and a hollow plunger adapted to travel through said hollow barrel, said hollow plunger having an outer close end and an inner end inserted in said hollow barrel through said open end portion, a closure seat being connected to said inner end of said hollow plunger so as to define a receiving cavity inside said hollow plunger, said closure seat having an entrance aperture positioned above said O-ring passage of said mounting seat, said entrance aperture being covered by a pusher member which is circumferentially connected with said entrance aperture in such a manner that said pusher member is detached to open said entrance aperture when a predetermined pound of urging force is applied to said pusher member;

thereby, when said closure seat of hollow plunger is intentionally pushed towards said mounting seat, said pusher member presses said tip head as well as said O-ring thereon to slide towards said needle hub and further compress said compression spring to store a resilient force, moreover when said O-ring is pressed to travel through of said O-ring passage, said resilient force of said compression spring increases to a force larger than said predetermined pound of urging force, so that the engagement of said O-ring between said ring groove of said tip head and said annular wall of said O-ring passage is released, and said resilient force stored in said compression spring upwardly pushes said tip head of said hollow needle to press against said pusher member until said entrance aperture is opened, so that said hollow needle, said pusher member and said compression spring are retracted into said receiving cavity of said hollow plunger.

2. A syringe as recited in claim 1 wherein said pusher member further comprises a pushing stud protruded towards said mounting seat, said pushing stud having a size adapted to enter said O-ring passage and directly apply pressing force onto said tip head of said needle when said plunger is inwardly pushed towards said mounting seat.

3. A syringe as recited in claim 2 wherein a plurality of pressing wings are spacedly extended from said pushing stud downwardly and adapted for inserting into said top end portion of said O-ring passage for pressing down said O-ring when said pusher member is pushed downwardly.

4. A syringe as recited in claim 2 wherein a sealing groove is provided around said inner end for holding a ring shaped sealing member thereon, said sealing member fitting in said clearance between an inner annular wall of said barrel and said sealing groove so as to ensure air tight and sealing effect of said plunger.

5. A syringe as recited in claim 3 wherein a sealing groove is provided around said inner end for holding a ring shaped sealing member thereon, said sealing member fitting in said clearance between an inner annular wall of said barrel and said sealing groove so as to ensure air tight and sealing effect of said plunger.

6. A syringe as recited in claim 2 wherein said closure seat further comprises a spacer which is disposed below a bottom surface of said closure seat and surrounded said pushing stud of said pusher member.

7. A syringe as recited in claim 3 wherein said closure seat further comprises a spacer which is disposed below a bottom surface of said closure seat and surrounded said pushing stud of said pusher member.

8. A syringe as recited in claim 4 wherein said closure seat further comprises a spacer which is disposed below a bottom surface of said closure seat and surrounded said pushing stud of said pusher member.

9. A syringe as recited in claim 5 wherein said closure seat further comprises a spacer which is disposed below a bottom surface of said closure seat and surrounded said pushing stud of said pusher member.

10. A syringe as recited in claim 6 wherein an air layer is defined between said bottom surface of said closure seat and said spacer and a plurality of air apertures are provided on said closure seat.

11. A syringe as recited in claim 7 wherein an air layer is defined between said bottom surface of said closure seat and said spacer and a plurality of air apertures are provided on said closure seat.

12. A syringe as recited in claim 8 wherein an air layer is defined between said bottom surface of said closure seat and said spacer and a plurality of air apertures are provided on said closure seat.

13. A syringe as recited in claim 9 wherein an air layer is defined between said bottom surface of said closure seat and said spacer and a plurality of air apertures are provided on said closure seat.

14. A syringe as recited in claim 10 wherein said spacer is integrally extended downwardly from a bottom end of said sea ling member to form a U-shaped body.

15. A syringe as recited in claim 11 wherein said spacer is integrally extended downwardly from a bottom end of said sealing member to form a U-shaped body.

16. A syringe as recited in claim 12 wherein said spacer is integrally extended downwardly from a bottom end of said sealing member to form a U-shaped body.

17. A syringe as recited in claim 13 wherein said spacer is integrally extended downwardly from a bottom end of said sealing member to form a U-shaped body.

18. A syringe as recited in claim 6 wherein said spacer comprises a deformable washer member and a rigid pusher ring integrally attached to a bottom surface of said washer member which is made of foaming material that is capable of reducing thickness under axial compression, said spacer having a thickness equal to a length of said pushing stud so as to positioned around the pushing stud by attaching a top side of said washer member to a bottom surface of said closure seat.

19. A syringe as recited in claim 7 wherein said spacer comprises a deformable washer member and a rigid pusher ring integrally attached to a bottom surface of said washer member which is made of foaming material that is capable of reducing thickness under axial compression, said spacer having a thickness equal to a length of said pushing stud so as to positioned around the pushing stud by attaching a top side of said washer member to a bottom surface of said closure seat.

20. A syringe as recited in claim 8 wherein said spacer comprises a deformable washer member and a rigid pusher ring integrally attached to a bottom surface of said washer member which is made of foaming material that is capable of reducing thickness under axial compression, said spacer having a thickness equal to a length of said pushing stud so as to positioned around the pushing stud by attaching a top side of said washer member to a bottom surface of said closure seat.

21. A syringe as recited in claim 9 wherein said spacer comprises a deformable washer member and a rigid pusher ring integrally attached to a bottom surface of said washer member which is made of foaming material that is capable of reducing thickness under axial compression, said spacer having a thickness equal to a length of said pushing stud so as to positioned around the pushing stud by attaching a top side of said washer member to a bottom surface of said closure seat.

* * * * *